United States Patent
Kokish et al.

[11] Patent Number: 5,873,817
[45] Date of Patent: Feb. 23, 1999

[54] ENDOSCOPE WITH RESILIENT DEFLECTABLE SECTION

[75] Inventors: Arkady Kokish, Orange; Gregory S. Konstorum, Stamford, both of Conn.

[73] Assignee: Circon Corporation, Goleta, Calif.

[21] Appl. No.: 854,882

[22] Filed: May 12, 1997

[51] Int. Cl.⁶ ........................................ A61B 1/00
[52] U.S. Cl. ............................ 600/143; 600/151
[58] Field of Search ................... 600/139, 140, 600/141, 142, 143, 144, 146, 150, 151

[56] References Cited

U.S. PATENT DOCUMENTS

| | | | |
|---|---|---|---|
| 3,270,641 | 9/1966 | Gosselin . | |
| 3,557,780 | 1/1971 | Sato | 128/4 |
| 3,799,151 | 3/1974 | Fukaumi et al. | 128/6 |
| 4,790,294 | 12/1988 | Allred, III et al. | 128/4 |
| 4,873,965 | 10/1989 | Danieli | 128/6 |
| 5,005,558 | 4/1991 | Aomori | 128/4 |
| 5,105,819 | 4/1992 | Wollschlager et al. | 128/662.06 |
| 5,220,911 | 6/1993 | Tamura | 600/142 X |
| 5,271,381 | 12/1993 | Ailinger et al. | 128/4 |

FOREIGN PATENT DOCUMENTS 63-136014  6/1988  Japan .

OTHER PUBLICATIONS

English Language translation of Japanese Patent No. 63–136014 dated Jun. 8, 1988 19 pages.

*Primary Examiner*—Beverly M. Flanagan
*Attorney, Agent, or Firm*—Perman & Green, LLP

[57] ABSTRACT

I An endoscope having a deflection control and a shaft connected to the deflection control. The shaft has a deflectable section operably connected to the deflection control by drive cables. The deflectable section comprises rigid rings and flexible connection members connecting the rings to each other. The connection members are comprised of a superelastic shape memory alloy. The connection members retain the deflectable section in a predetermined shape. The connection members can be resiliently bent to bend the deflectable section without permanent deformation of the connection member over a working life of the endoscope.

26 Claims, 7 Drawing Sheets

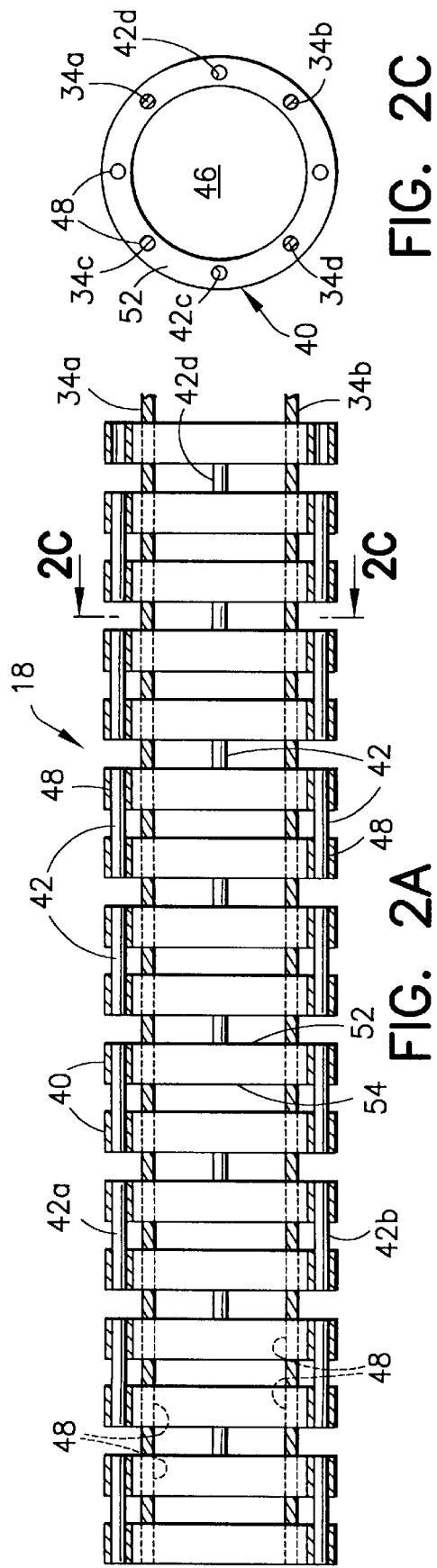
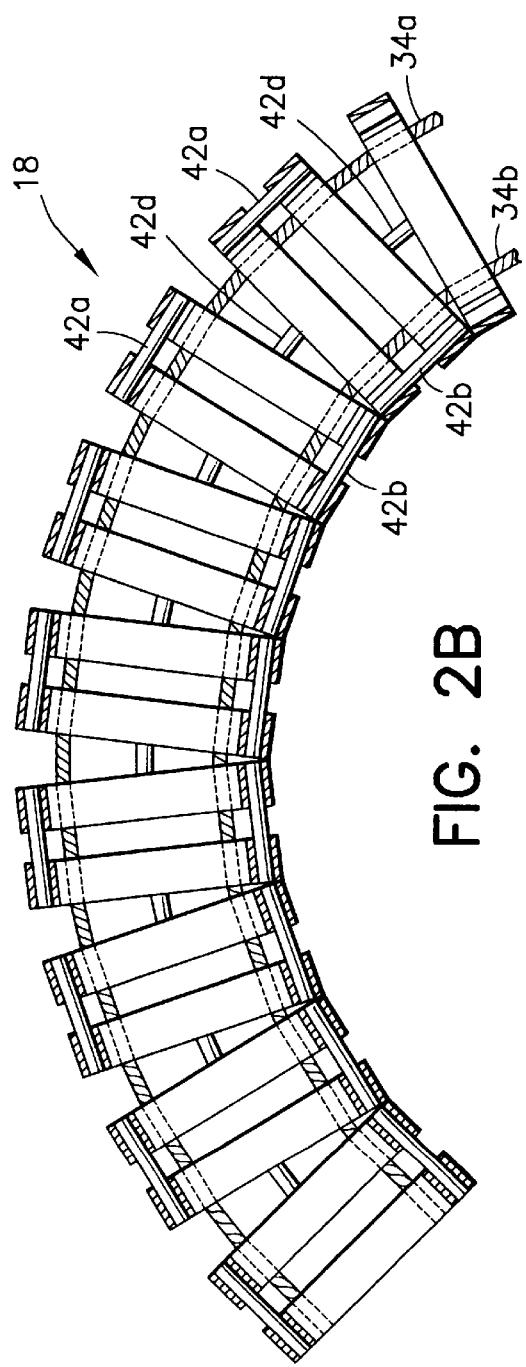
FIG. 2C
FIG. 2A
FIG. 2B

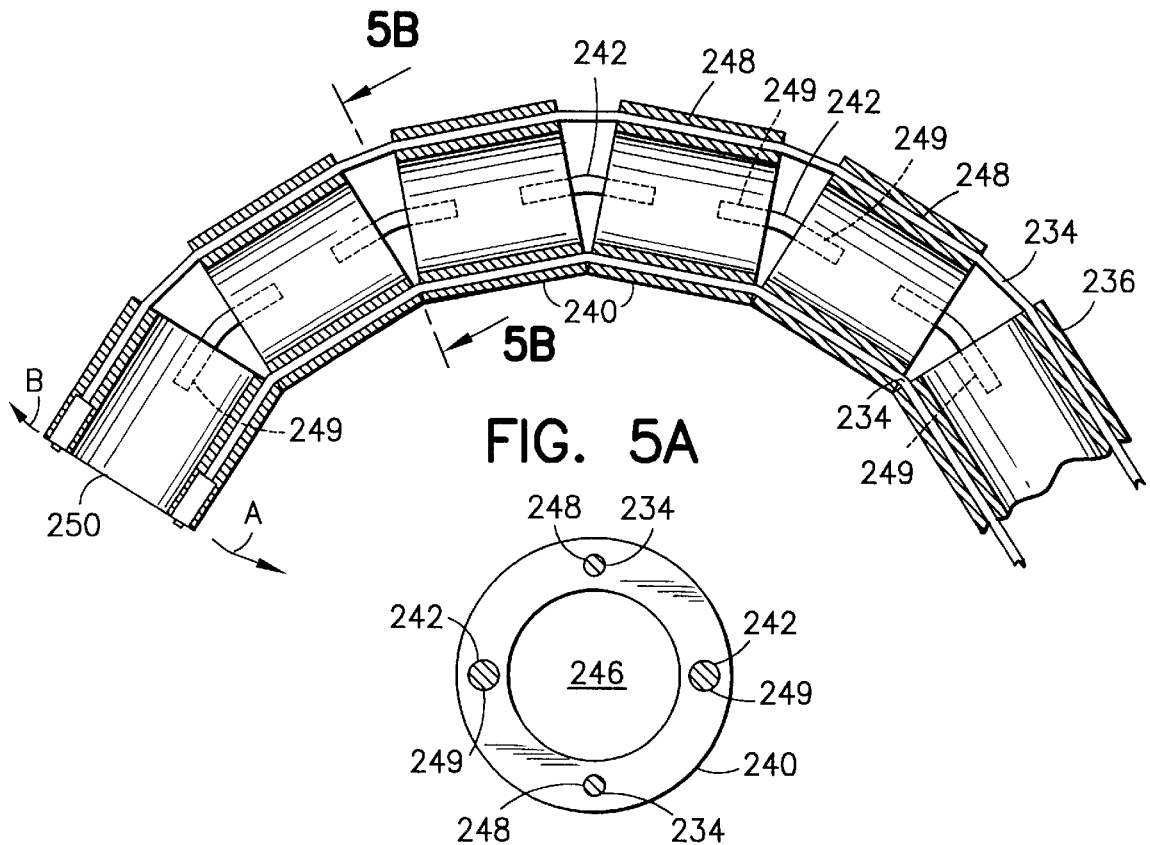
FIG. 5A
FIG. 5B
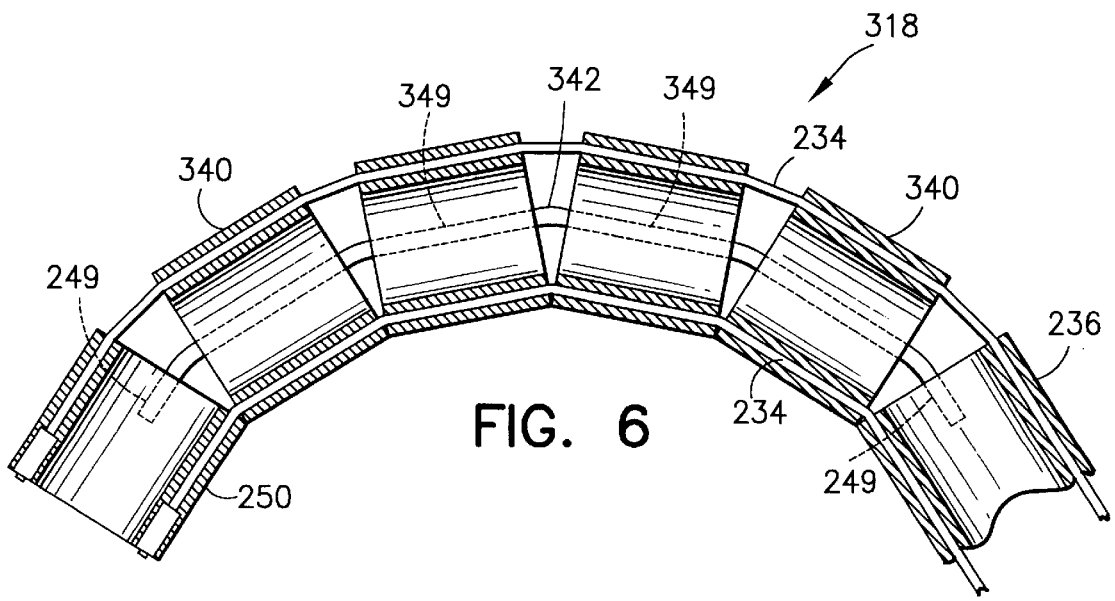
FIG. 6

ENDOSCOPE WITH RESILIENT DEFLECTABLE SECTION

BACKGROUND OF THE INVENTION

1. Field of the Invention

The present invention relates to medical instruments and, more particularly, to an endoscope with a deflectable section.

2. Prior Art

U.S. Pat. No. 5,005,558 discloses an endoscope with ring link members connected by flexible connection members. Various materials to make the flexible connection members are disclosed along with different shapes including a coil, a wire, a tube, and a stick or rod. Various other types of endoscopes with deflectable sections are also known in the art.

SUMMARY OF THE INVENTION

In accordance with one embodiment of the present invention, an endoscope is provided having a deflection control and a shaft connected to the deflection control. The shaft has a deflectable section operably connected to the deflection control by drive cables. The deflection section comprises rigid rings and flexible connection members connecting the rings to each other. The connection members are comprised of a superelastic shape memory alloy. The connection members retain the deflection section in a predetermined shape. The connection members can be resiliently bent to bend the deflection section without permanent deformation of the connection members over a working life of the endoscope.

In accordance with another embodiment of the present invention, an endoscope is provided having a deflection control and a shaft connected to the deflection control. The shaft has a deflectable section with rigid rings. The improvement comprises flexible connection members connecting the rings to each other. The flexible connection members are comprised of a superelastic shape memory alloy. The flexible connection members have a naturally straight shape and each of the connection members are fixedly connected to pairs of the rings.

In accordance with another embodiment of the present invention, an endoscope is provided having a deflection control and a shaft connected to the deflection control. The shaft has a deflection section with rigid rings. The improvement comprises a plurality of flexible connection members connecting the rings to each other. The flexible connection members are comprised of a superelastic shape memory alloy. Each of the connection members are connected to its corresponding rings.

In accordance with another embodiment of the present invention, an endoscope is provided having a deflection control and a shaft connected to the deflection control. The shaft has a deflection section operably connected to the deflection control by drive cables. The deflection section comprises rigid rings and stiffening members. The rigid rings are movably connected to each other in series. The stiffening members extend through holes of substantially all of the rings. The stiffening members have an elongate shape and are comprised of a superelastic alloy. The rings are longitudinally movable along the stiffening members.

BRIEF DESCRIPTION OF THE DRAWINGS

The foregoing aspects and other features of the invention are explained in the following description, taken in connection with the accompanying drawings, wherein:

FIG. 2A is a cross-sectional view of the deflection section of the endoscope shown in FIG. 1;

FIG. 2B is a cross-sectional view of the deflection section shown in FIG. 2A with the deflection section being deflected into a curved shape;

FIG. 2C is a cross-sectional view of the deflection section shown in FIG. 2A taken along line 2C—2C;

FIG. 5A is a schematic cross-sectional view of a deflection section of an alternate embodiment of the present invention;

FIG. 5B is a cross-sectional view of the deflection section shown in FIG. 4A taken along line 4B—4B;

FIG. 6 is a schematic cross-sectional view of an alternate embodiment of an endoscope deflection section incorporating features of the present invention.

DETAILED DESCRIPTION OF THE PREFERRED EMBODIMENTS

Figure 1:
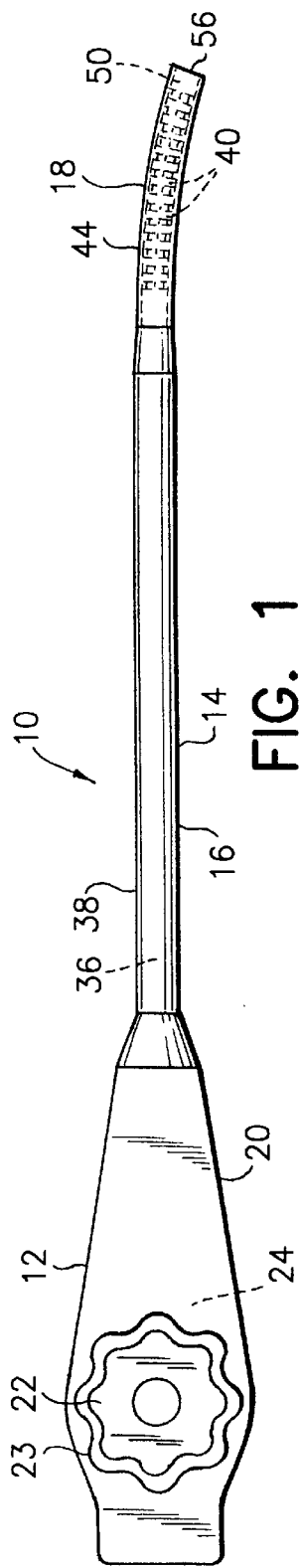
FIG. 1 is a side view of an endoscope incorporating features of the present invention.

Referring now to FIG. 1, there is shown an elevational side view of an endoscope 10 incorporating features of is the present invention. Although the present invention will be described with reference to the embodiments shown in the drawings, it should be understood that features of the present invention can be embodied in various different forms of alternate embodiments. Features of the present invention can be embodied in various different types of endoscopes. In addition, any suitable size, shape or type of elements or materials could be used.

The endoscope 10 generally comprises a deflection control 12 and a shaft 14 connected to the deflection control. The shaft 14 has a rigid section 16 and a deflectable section 18 at its distal end. However, in alternate embodiments, any suitable type of shaft, with a deflectable section as described below, could be provided. The deflection control 12 includes a housing 20, two user actuated knobs 22, 23, and a drive system 24 located inside the housing 20. The knobs 22, 23 are connected to the drive system 24. The drive system 24 is connected to rear ends of four drive wires or cables 34a, 34b, 34c, 34d that extend through the shaft 14 (see FIGS. 2A and 2C). The drive system 24 is adapted to pull and release the wires 34 when the knobs are rotated. Various different types of drive systems are well known in the art and, therefore, the drive system 24 is not described further. The drive cables 34 extend from the drive system 24 into the rigid section 16 of the shaft 14. The rigid section 16 has a tube frame 36 and an outer cover 38. In alternate embodiments any suitable type of rigid section could be provided. Alternatively, a rigid section need not be provided. The cables 34 extend is through the rigid section 16 up to and into the deflectable section 18.

Referring also to FIGS. 2A and 2C the deflectable section 18 includes general ring shaped rings or link members 40, flexible connection members 42, and a protective cover 44 (see FIG. 1). The cover 44 is not shown in FIGS. 2A—2C for ease of illustration only. In the embodiment shown, the rings 40 are comprised of a rigid material, such as metal. The rings 40 are identical to each other with a center aperture 46 and eight smaller through-holes 48. The rings 40 are arranged in series. The center apertures 46 thus form a center channel for location or passage of instruments or tools (not shown). The f our cables 34a, 34b, 34c, 34d movably pass through four of the holes 48 in each ring. The distal ends of the cables 34 are fixedly attached to either the last distal ring or, alternatively, to an end member 50 attached to the last distal ring. The four other holes 48 in a majority of the rings 40 have the flexible connection members 42 mounted therein. More specifically, each ring (except for the first and last rings in the series) has a first set of two of the connection members 42 extending from a first rear end 52 of the ring and a second set of the two other connection members 42 extending from an opposite second front end 54 of the ring. In the embodiment shown, the two connection members 42 of the first set are offset from each other on opposite sides of the rear end 52. The two connection members 42 of the second front set are also offset from each other on opposite sides of the front end 54. In addition, the two sets are offset from each other about 90° relative to the center axis of the ring's center aperture 46. Thus, pairs of the rings are formed by the connection members 42a, 42b with the pairs of rings also being connected to each other by the is other connection members 42c, 42d.

The connection members 42 are identical to each other. The connection members are preferably comprised of a shape memory alloy, such as tinel or nitinol. More specifically, the shape memory alloy is used for its superelastic properties and its ability to resiliently return to its natural or home position. Thus, the term "superelastic alloy" is used below to denote this material. In this embodiment, the connection members 42 are solid pins or rods that are fixedly mounted in the holes 48 by suitable means, such as adhesive. The connection members 42 have a naturally straight shape as seen in FIG. 2A. This provides the deflection section 18 with a naturally straight shape as seen in FIG. 2A. In alternate embodiments, the deflection section could have a naturally non-straight shape, such as if the connection of the connection members 42 to the rings 40 is different or if the deflection section is biased into a non-straight shape. The cables 34 can be moved by the deflection control 12 to bend the deflection section 18 into a desired shape and position. This allows the user to relocate the distal tip 56 (see FIG. 1) to a desired position in the patient's body.

Referring also to FIG. 2B, the deflection section 18 is shown in a bent position. In the position shown, the knobs 22, 23 of the deflection control 12 have been moved by the user to retract the two cables 34b and 34d and reciprocally extend the two cables 34a and 34c. The connection members 42a and 42b have remained straight. However, the connection members 42c and 42d have bent. Because the connection members are comprised of a superelastic alloy, they are able to resiliently bend without permanent deformation and without fatigue. Thus, over the working life of the endoscope 10, which may be is decades, the connection members 42 will not break or lose significant resilience from fatigue normally associated with stress and strain in metal springs from repeated deformation. The connection members 42, although resiliently bendable, do not significantly expand or contract. This is because of their solid rod or pin shape. This adds to a predictable and precise deflection at the deflection section. Thus, as seen in FIG. 3B, although connection members 42a are in tension, they do not expand. Likewise, although connection members 42b are in compression, they do not compress. The connection members 42 provide bending while also providing fixed constraint among some of the rings from compression or expansion. Thus, the connection members of the present invention cannot be stretched like the coil springs in U.S. Pat. No. 5,005,558. In addition, the connection members of the present invention do not fatigue over the working life of the endoscope as can happen to the mere metal connection members in U.S. Pat. No. 5,005,558.

One of the features of the deflection section 18 is its ability to be used to move or push body tissue inside the patient. More specifically, because the connection members 42 do not longitudinally expand or compress, they provide the deflection section 18 with a reconfigurable, but substantially rigid shape. Because the deflection section 18 is attached to the rigid section 16 of the shaft, the user can move the rigid section 16 to move the deflection section 18 and its distal tip 56 into a desired position. This can be accomplished without substantial risk of nearby patient tissue changing the shape of the deflection section 18 as the tissue presses against the deflection section. Therefore, it is easier and faster for the user to position the distal tip 56 at its desired location without significant interference or distortion from the patient's body tissue.

Figure 3A:
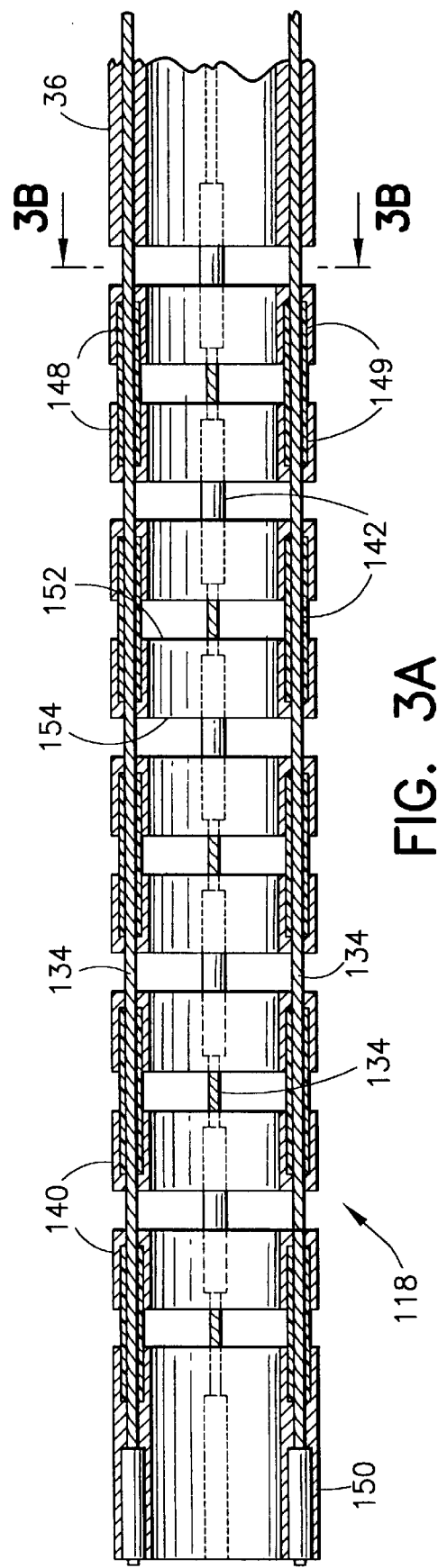
FIG. 3A is a schematic cross-sectional view of a deflection section in an alternate embodiment of the present invention.
Figure 3B:
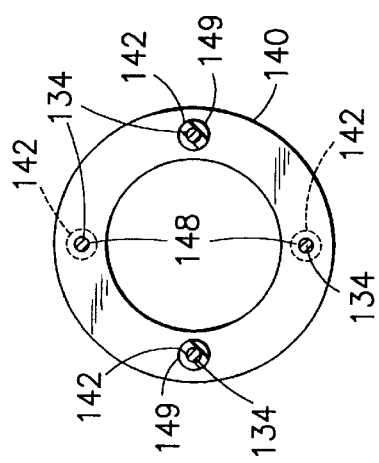
FIG. 3B is a cross-sectional view of the deflection section shown in FIG. 3A taken along line 3B—3B.

Referring now to FIGS. 3A and 3B, an alternate embodiment of a deflection section 118 is shown. Similar to FIGS. 2A—2C, the deflection section 118 in FIGS. 3A and 3B is shown without its protective cover for illustration purposes only. The deflection section 118 includes rigid rings or links 140, connection members 142, and distal end member 150. Four drive cables or wires 134 extending through the end of the rigid shaft frame 36, through the rings 140, and are fixedly attached to the distal end member 150. In this embodiment the rings 140 have only four smaller through-holes 148. The holes 148 each have an enlarged counter-bore section 149; two on each end 152, 154. The connection members 142 have a general solid tube or cylinder shape and are comprised of a superelastic alloy. Two connection members 142 extend between each ring 140. Ends of the connection members 42 are located in opposing enlarged counter-bore sections 149 of the adjacent rings 140 and stationarily fixed in the holes 148 by suitable means, such as adhesive. The drive cables 134 extend through the centers of the connection members 142. The connection members 142 keep the deflection section 118 in a straight shape, but can be bent when the cables 134 push or pull on the distal end member 150 to bend the deflection section 118.

Figure 3C:
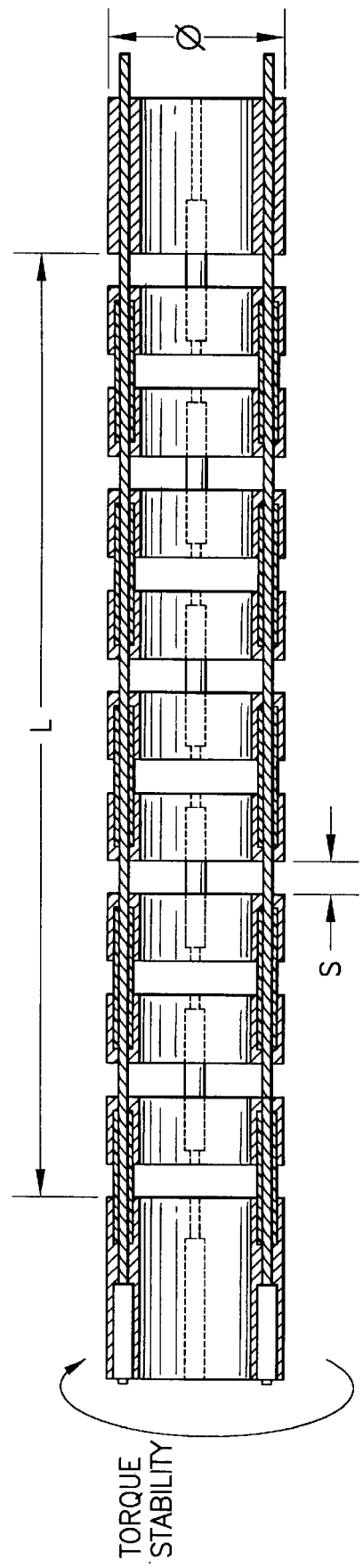
FIG. 3C is a schematic cross-sectional view of the embodiment shown in FIG. 3A.
Figure 3D:
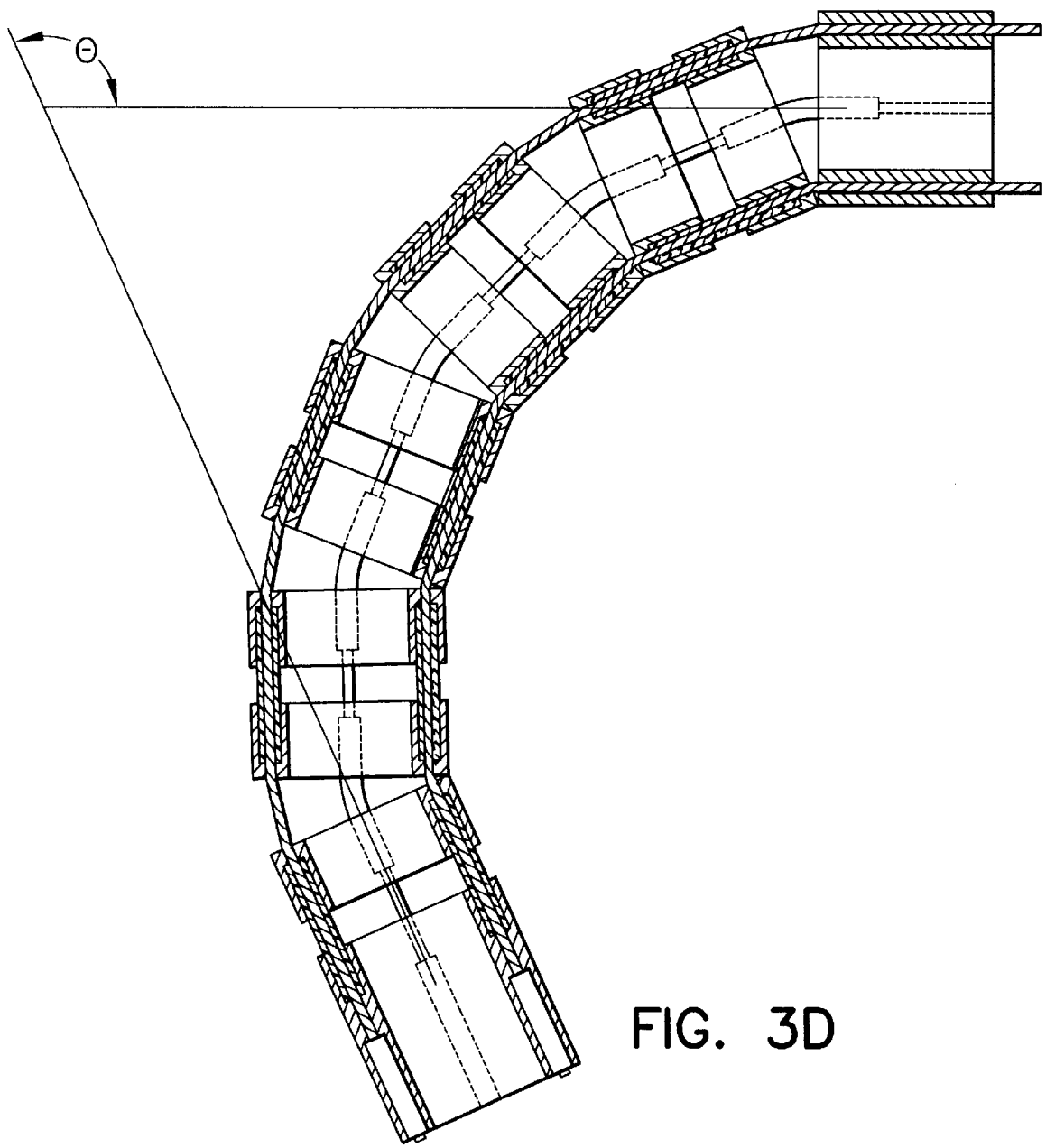
FIG. 3D is a cross-sectional view of the deflection section in FIG. 3C with the deflection section being deflected into a curved shape.
Figure 4A:
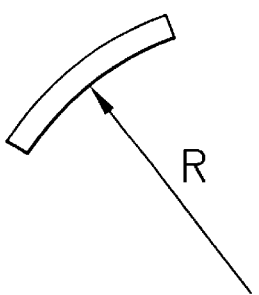
FIG. 4A is a view of a single rod connecting member bent into a bent shape at a radius R.

Referring also to FIG. 3C and 3D, the intended application of the instrument usually dictates the diameter φ, length L, and the desired deflection angle θ. A designer will then need to create an assembly with spacing s which, over several rings, will create the desired deflection angle θ. The use of coiled springs as flexible connection members, such as disclosed in U.S. U.S. Pat. No. 5,005,558, gives rise to designs that are not torque stable. The arrow C on FIG. 3C shows a torque invoked on the most distal member of the deflection assembly causing motion around the centerline. Resisting this rotational motion is the connection at each successive ring (which is the flexible connection member) through to the proximal ring. If this rotary motion is excessive, the coiled spring design exhibits poor toque stability. Deflection assemblies with poor torque stability are not practical. U.S. Pat. No. 5,005,558 also disclosed use of rods as flexible connection members. FIG. 3E shows a rod bent to radius R. It is obvious that R is inversely related to spacing s and this in turn determines the overall length L for a deflection assembly designed for angle θ. The geometry of the rod and its material of construction has a profound effect on the overall design. Using steel as an example (all materials listed in Table 1 of U.S. Pat. No. 5,005,558 will exhibit similar limitations), shown in FIG. 4A is the tensile stress strain relationship for a typical alloy of steel used in this application. Practical designs limit the allowable strain to about 0.4%. A designer faced with this constraint will choose to either:

a) use thin connection rods which can bend to radius R and thus meet the requirements of overall length L and deflection angle θ (Designs with thin rods are not robust and suffer the aforementioned torque stability problem); or b) use thicker rods and reduce R to be within 0.4% strain and employ more rings (the overall length of the deflection assembly will grow).

Figure 4B:
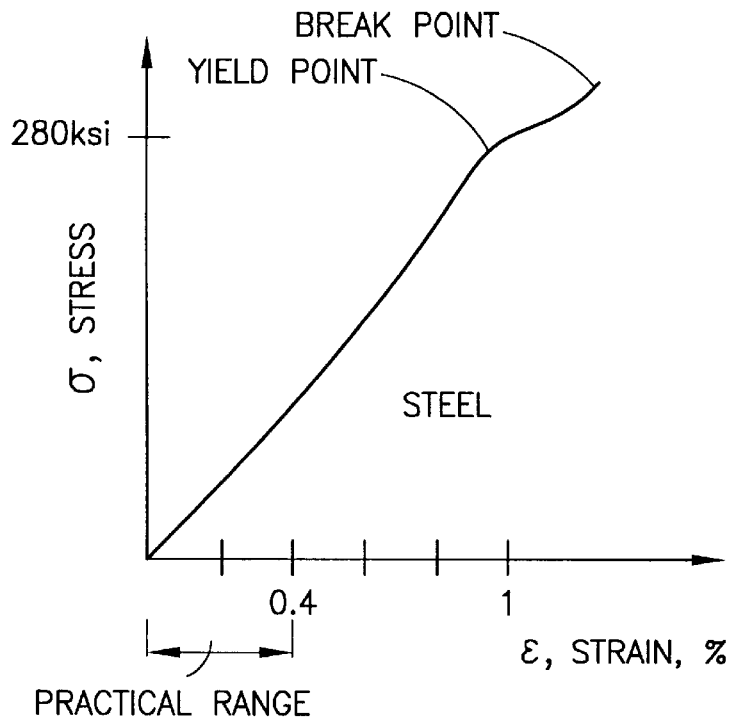
FIG. 4B is a stress and strain graph diagram for a steel rod connecting member.

Neither (a) nor (b) are practical. However, the present invention uses materials which exhibit superelasticity, such as Titanium-Nickel and copper based alloys. When is these materials are used, then the allowable strain level is increased by an order of magnitude to about 4%. The stress strain relationship for this material is shown in FIG. 4B. Most endoscopes are designed for several years of service life. Thus, the limit of 4% allowable strain can provide this long service life. If longevity is not important, and one desires to approach the extremes of mechanical performance, then the allowable strain can be raised to about 8%.

Deflection assemblies produced with superelastic materials will have the following attributes:

1) Be robust; they will resist deformation caused by external forces other than the drive cables. The "stiffness" feature is useful in medical ultrasound imaging where forces are needed to achieve acoustic coupling with tissue.

2) Be shorter than designs that use conventional materials. The order of magnitude increase in allowable strain will, in simple terms, result in a commensurate decrease in deflection assembly length.

3) Have lower activation forces. For steel, the stress strain relationship is steep (typical modulus of 28 msi) which means higher forces for higher articulation angle. This same relationship for superelastic material is relatively flat which reduces the amount of force needed to achieve a deflection angle.

Figure 4C:
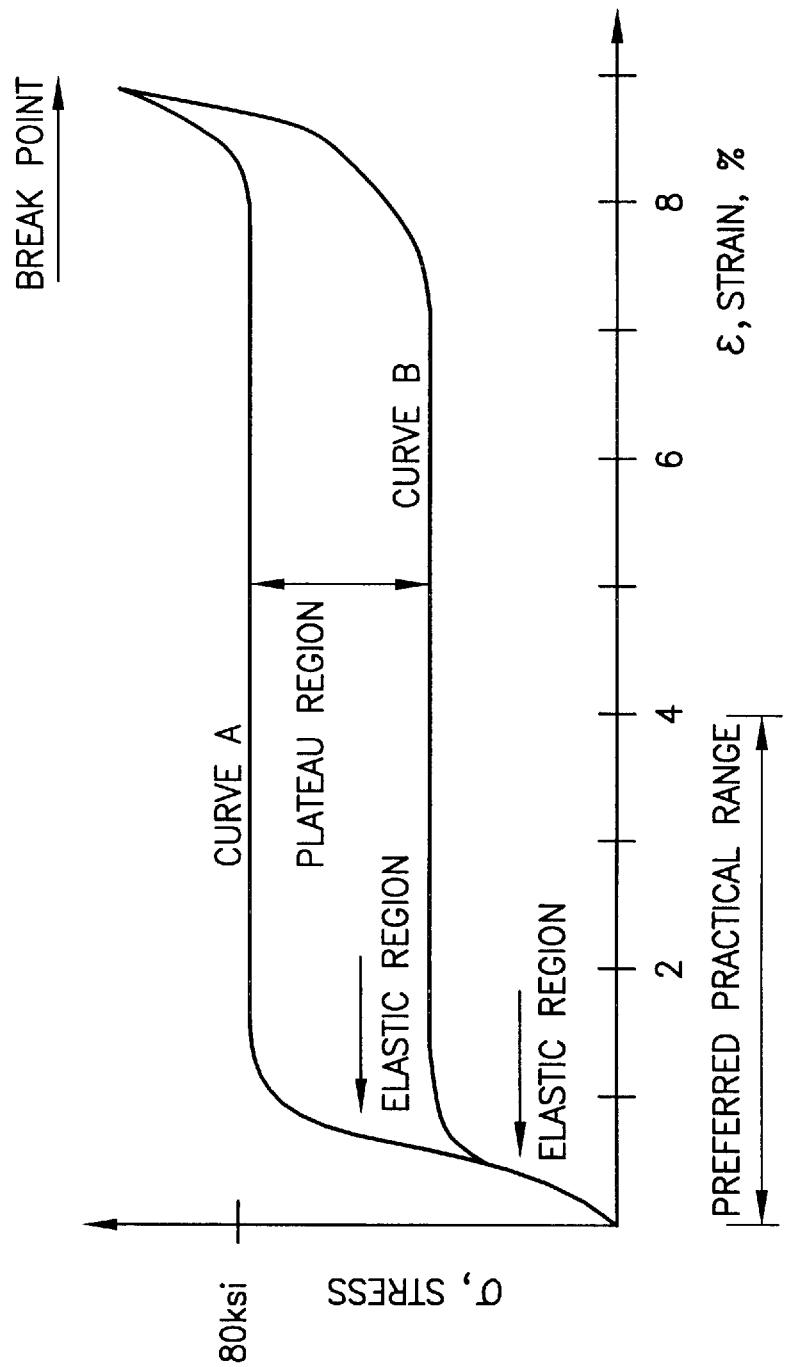
FIG. 4C is a stress and strain graph diagram for superelastic rod connecting members.

The present invention provides the capability to create stiff, torque stable deflection assemblies with superelastic parts. Referring to FIG. 4C, for selection of different activation forces, there are a variety of superelastic material stress strain relationships that can be selected. There are an infinite number of possible curves, each identified by its "conversion temperature"; an attribute well known to producers of shape memory alloys. Each curve has an elastic region in which the modulus is similar to other metals (e.g. 28 msi for steel) and a plateau region in which the modulus is nearly zero. The activation force for an endoscope designed with superelastic material is the sum of the elastic region and the plateau region up to the design strain level. One can see that the superelastic material depicted in Curve A will yield a higher activation force than the superelastic material depicted in Curve B. Preferably, stiffness is achieved by selecting a superelastic material with a stress/strain curve similar to Curve A in which most of the stress is picked up at a low strain level. If one were to use a superelastic material with a stress/strain curve similar to Curve B. the deflection assembly will not be as stiff at low deflections, but will be more resistant to breakage at high strain levels.

Referring now to FIGS. 5A and 5B, another alternate embodiment of a deflection section 218 is shown without its protective cover. In this embodiment the deflection section is designed to bend in only two directions as indicated by arrows A and B. The deflection section 218 has rigid rings 240, connecting members 242, and a distal end member 250. In this embodiment, only two drive cables 234 are provided. The cables 234 movably extend through the end of the rigid shaft frame 236, through two through-holes 248 in each ring 240, and are fixedly attached to the distal end member 250. The rings 240 is each have a center aperture 246, the two through-holes 248, and four seats 249. Two of the seats 249 are provided on each side of each ring 240. The seats 249 are also provided at ends of the frame 236 and the distal end member 250. The connection members 242, made of a superelastic alloy, are fixedly attached in the seats 249. Thus, extension and retraction of the two cables 234 moves the distal end member in either direction A or direction B. but the connection members 242 help to restrain movement in other directions.

Referring also to FIG. 6, another alternate embodiment is shown. This embodiment is similar to the deflection section shown in FIG. 5A. However, the deflection section 318 has only two elongate rod shaped connecting members 342 (only one of which is shown). In addition, the rings 340 have the seats 349 provided as through-holes. The connecting members 342 are preferably fixedly attached to the rings 340 in each of the seats 349 and fixedly mounted in the seats 249 of the frame 236 and distal end member 250, such as by adhesive. This type of embodiment may be easier to assemble than the multiple small connection members shown in FIG. 5A. Alternate embodiments could obviously be devised by people skilled in the art to include any suitable number, shape, size and location of the superelastic alloy connecting members between and among the rigid links of the deflectable section.

Figure 7:
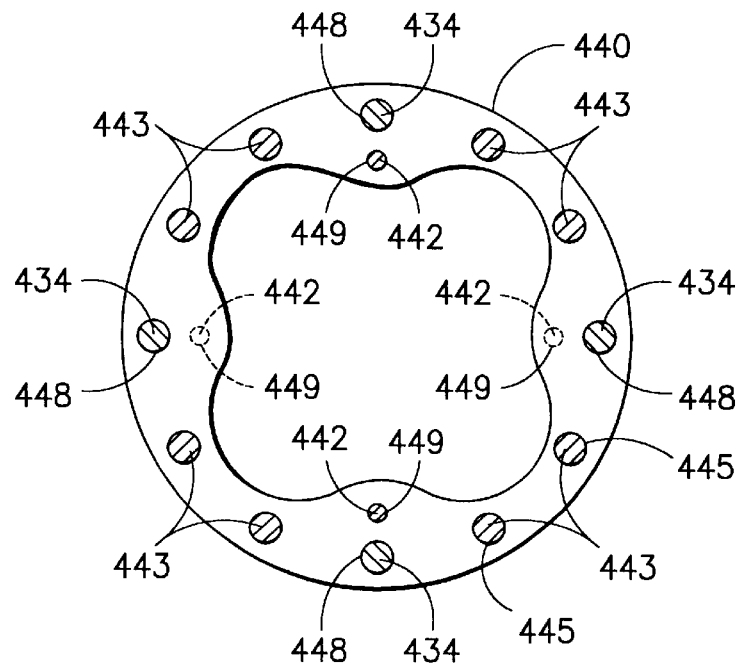
FIG. 7 is a cross-sectional view of an alternate embodiment of an endoscope deflection section incorporating features of the present invention.

Referring now to FIG. 7 another alternate embodiment of the deflection section will be described. In this embodiment, the deflection section has rigid rings 440 (only one of which is shown), alternating pairs of connection members 442, four deflection control wires 434, and eight stiffening rods 443. Each ring 440 has four control wire through-holes 448. The control wires 434 movably pass through the wire through-holes 448. Each ring 440 has four connection member seats 449; two on each side. Each seat 449 has one or the connection members 442 fixedly mounted therein. The connection members 442 are comprised of superelastic alloy as pins with small diameters. The small diameters have been selected because it has been discovered that the small diameter pins provide an increased working life, longer than larger diameter pins, for the deflection section before a failure occurs. However, in making the diameter of the connection members 442 smaller, stiffness and torque stability of the deflection section was reduced. To increase stiffness and torque stability of the deflection section, the stiffening rods 443 have been added. The rods 443 are preferably comprised of superelastic alloy. The rods 443 pass through all of the rings 440 through eight holes 445. More specifically, the rods 443 are movably located in the holes 445. More or less than eight stiffening rods could be used. Preferably, the stiffening rods need only be secured at one place in the ring structure, such as at the distal end member or at the rigid shaft frame. However, in an alternate embodiment, the rods 443 need only be entrapped between the distal end member and the rigid shaft frame. Thus, the stiffening rods 443 float relative to the rings 440, but exert a stiffening force on the rings to bias the rings at a home position. Preferably, the home position is a straight shape of the deflection section. The combination of superelastic connection members 442 and superelastic stiffening members 443 provide a resilient deflection section with an improved working life. In alternate embodiments the stiffening members 443 could have any suitable cross-sectional shape, such as rectangular or tube. The stiffening members could also be located at any suitable pattern relative to the control wires and/or the connection members. The central aperture for the rings could also have any suitable shape. In other alternate embodiments, the floating stiffening members could be used with other types of ring connection systems, such as pinned or mating rings. The use of floating stiffening members made of superelastic alloy is not intended to be limited to use with only superelastic connection members.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. An endoscope having a deflection control and a shaft connected to the deflection control, the shaft having a deflectable section operably connected to the deflection control by drive cables, the deflection section comprising:
   rings; and
   flexible connection members connecting the rings to each other, the connection members being comprised of a superelastic alloy, wherein the connection members retain the deflection section in a predetermined shape, and wherein the connection members can be repeatedly resiliently bent to bend the deflection section without permanent deformation of the connection members over a working life of the endoscope because of superelastic properties of the superelastic alloy.

2. An endoscope as in claim 1 wherein the flexible connection members have a general pin shape.

3. An endoscope as in claim 2 wherein the flexible connection members have a naturally straight shape.

4. An endoscope as in claim 3 wherein the flexible connection members are individually connected between two rings to form pairs of rings.

5. An endoscope as in claim 4 wherein at least two connection members connect the pairs of rings to each other.

6. An endoscope as in claim 5 wherein a majority of rings have at lest four connection members connnected thereto with two on each side of the rings.

7. An endoscope as in claim 6 wherein the majority of the rings each have eight holes therethrough with the at least four connection members in four of the holes and the drive cables in the four holes.

8. An endoscope as in claim 1 wherein the flexible connection members have a general straight tube shape.

9. An endoscope as in claim 8 wherein the flexible have holes with enlarged counter-bore sections, and the flexible connection members are located in the enlarged counter-bore sections of the holes.

10. An endoscope as in claim 9 wherein the drive cables pass through a center aperture of the tube shape of the flexible connection members.

11. An endoscope as in claim 1 wherein the flexible connection members have a general straight wire shape and extend along substantially the entire length of the deflection section.

12. An endoscope as in claim 1 further comprising stiffening members extending through holes of the rings, the stiffening members having an elongate shape and being comprised of a superelastic alloy, wherein the rings are longitudinally movable along the stiffening members.

13. An endoscope as in claim 1 wherein the superelastic alloy allows a strain of the connection members of at least about 4% without permanent deformation of the connection members.

14. In an endoscope having a deflection control and a shaft connected to the deflection control, the shaft having a deflectable section with rigid rings, wherein the improvement comprises:
   flexible connection members connecting the rings to each other, the flexible connection members being comprised of a superelastic alloy, wherein the flexible connection members have a naturally straight column shape and each connection member is fixedly connected between two of the rings with one end of the column shape connected to one of the two rings and a spaced opposite end of the column shape connected to another of the two rings, and wherein a middle of the column shape is adapted to be repeatedly resiliently bent without permanent deformation because of superelastic properties of the superelastic alloy and, provide a biasing force to return the connection member back to its naturally straight column shape.

15. An endoscope as in claim 14 wherein the flexible connection members have a general solid pin shape.

16. An endoscope as in claim 14 wherein pairs of rings have at least two connection members between each pair of rings.

17. An endoscope as in claim 14 wherein a majority of the rings have at least four connection members connected thereto with two on each of two opposite sides of the rings.

18. An endoscope as in claim 17 wherein the majority of the rings each have eight holes therethrough with the at least four connection members in four of the holes and the drive cables in the other four holes.

19. An endoscope as in claim 14 wherein each ring has only four flexible connection members connected to it, two of the flexible connection members being located on each of two opposite sides of each ring.

20. An endoscope as in claim 14 wherein the flexible connection members have a general straight tube shape.

21. An endoscope as in claim 20 wherein the rings have holes with enlarged counter-bore sections, and the flexible connection members are located in the enlarged counter-bore sections of the holes.

22. An endoscope as in claim 14 further comprising stiffening members extending through holes of the rings, the stiffening members having an elongate shape and being comprised of a superelastic alloy, wherein the rings are longitudinally movable along the stiffening members.

23. An endoscope as in claim 14 wherein the superelastic alloy allows a strain of the connection members during bending of over 1% without permanent deformation of the connection members.

24. In an endoscope having a deflection control and a shaft connected to the deflection control, the shaft having a deflection section with rigid rings, wherein the improvement comprises:

a plurality of flexible connection members connecting the rings to each other, the flexible connection members being comprised of a superelaslic shape memory alloy, wherein at least two of the connection members are connected to a majority of the rings.

25. An endoscope as in claim 24 further comprising stiffening members extending through holes of the rings, the stiffening members having an elongate shape and being comprised of a superelastic alloy, wherein the rings are longitudinally movable along the stiffening members.

26. An endoscope having a deflection control and a shaft connected to the deflection control, the shaft having a deflectable section operably connected to the deflection control by drive cables, the deflection section comprising:

rigid rings movably connected to each other in series, the rings having holes therein; and stiffening members extending through the holes of all of the rings, the stiffening members having an elongate shape and being comprised of a superelastic alloy, wherein a plurality of the rings are longitudinally movable along the stiffening members.

* * * * *